United States Patent
Kuhn

(10) Patent No.: US 9,417,302 B2
(45) Date of Patent: Aug. 16, 2016

(54) THERAPEUTIC APPARATUS FOR TREATING A SUBJECT USING MAGNETIC NANOPARTICLES

(75) Inventor: Michael Harald Kuhn, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 507 days.

(21) Appl. No.: 13/202,435

(22) PCT Filed: Feb. 22, 2010

(86) PCT No.: PCT/IB2010/050764
§ 371 (c)(1),
(2), (4) Date: Sep. 1, 2011

(87) PCT Pub. No.: WO2010/097749
PCT Pub. Date: Sep. 2, 2010

(65) Prior Publication Data
US 2011/0306870 A1    Dec. 15, 2011

(30) Foreign Application Priority Data
Feb. 27, 2009   (EP) .................................. 09153915

(51) Int. Cl.
*A61H 1/00*    (2006.01)
*G01R 33/48*   (2006.01)
(Continued)

(52) U.S. Cl.
CPC .......... *G01R 33/4804* (2013.01); *A61B 5/0515* (2013.01); *A61N 1/406* (2013.01); *A61N 2/02* (2013.01); *A61N 7/02* (2013.01); *G01R 33/4808* (2013.01); *A61B 5/01* (2013.01); *A61B 5/055* (2013.01); *A61B 5/7207* (2013.01); *A61B 5/7267* (2013.01); *A61B 17/2251* (2013.01); *A61B 18/18* (2013.01); *A61B 18/1815* (2013.01);
(Continued)

(58) Field of Classification Search
CPC .................................. A61N 7/02; A61N 7/00
USPC .............................................................. 601/3
See application file for complete search history.

(56) References Cited

U.S. PATENT DOCUMENTS 6,530,994 B1   3/2003   Mahawili
7,999,161 B2 * 8/2011   Oraevsky et al. ............. 424/489
(Continued)

FOREIGN PATENT DOCUMENTS

WO   WO03022360    3/2003
WO   WO2007015179  2/2007
(Continued)

OTHER PUBLICATIONS

O.M. Al-Bataineh et al., "MR Thermometry Characterization of Hyperthermia Ultrasound Array Designed Using K-Space Computational Method" Biomedical Engineering Online, Oct. 2006.
(Continued)

*Primary Examiner* — Tse Chen
*Assistant Examiner* — Hien Nguyen

(57) ABSTRACT

A therapeutic apparatus for treating a subject comprising: a first heating means adapted for heating a first region of the subject, a first control means for controlling the power directed into the first region by the first heating means such that the power stays below a threshold value, a particle heating means adapted for heating magnetic nanoparticles within a second region of the subject using a time varying magnetic field, wherein the first region comprises the second region.

11 Claims, 7 Drawing Sheets

(51) Int. Cl.

| | | |
|---|---|---|
| *A61B 5/05* | (2006.01) | |
| *A61N 1/40* | (2006.01) | |
| *A61N 2/02* | (2006.01) | |
| *A61N 7/02* | (2006.01) | |
| *A61B 5/01* | (2006.01) | |
| *A61B 5/055* | (2006.01) | |
| *A61B 17/225* | (2006.01) | |
| *A61B 18/18* | (2006.01) | |
| *A61B 17/00* | (2006.01) | |
| *A61B 18/00* | (2006.01) | |
| *A61B 19/00* | (2006.01) | |
| *A61N 5/02* | (2006.01) | |
| *A61B 5/00* | (2006.01) | |

(52) U.S. Cl.
CPC .................. *A61B2017/00084* (2013.01); *A61B 2018/00666* (2013.01); *A61B 2018/00678* (2013.01); *A61B 2018/00791* (2013.01); *A61B 2019/5236* (2013.01); *A61N 5/02* (2013.01); *G01R 33/4814* (2013.01)

(56) References Cited

U.S. PATENT DOCUMENTS

| | | | |
|---|---|---|---|
| 2007/0168001 | A1 | 7/2007 | Xiang et al. |
| 2007/0196281 | A1 | 8/2007 | Jin et al. |
| 2007/0219442 | A1* | 9/2007 | Aletras et al. .................. 600/410 |
| 2008/0045865 | A1* | 2/2008 | Kislev ................. 601/3 |
| 2008/0213382 | A1* | 9/2008 | Ivkov et al. ................... 424/497 |

FOREIGN PATENT DOCUMENTS

| | | |
|---|---|---|
| WO | WO2007027620 | 3/2007 |
| WO | WO2007035871 | 3/2007 |
| WO | WO2008001155 | 1/2008 |
| WO | WO2008023314 | 2/2008 |
| WO | WO2008131306 | 10/2008 |

OTHER PUBLICATIONS

G.F. Goya et al., "Magnetic Nanoparticles for Cancer Therapy", Current Nanoscience 4, 2008, pp. 1-16.

* cited by examiner

THERAPEUTIC APPARATUS FOR TREATING A SUBJECT USING MAGNETIC NANOPARTICLES

FIELD OF THE INVENTION

The invention relates to a therapeutic apparatus and a computer program product for treating a subject using the heating of magnetic particles.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduced the need for hysterectomy procedures.

To selectively treat tissue, a focused ultrasonic transducer can be used to focus the ultrasound on a particular treatment volume. The transducer is typically mounted within a medium, such as degassed water, that is able to transmit ultrasound. Actuators are then used to adjust the position of the ultrasonic transducer and thereby adjust the tissue region that is being treated. However, it is often not possible to focus ultrasound beams in the vicinity of bone and tissue boundaries and also in the vicinity of air and tissue boundaries. This prevents ultrasound treatment of many regions of the body. Examples are the ablation of tissue from the prostate with standard transducer arrays and the treatment of tumors in the lungs.

US patent application US2008/0045865 discloses exposing nanoparticles to electromagnetic radiation, excluding radio-frequency radiation, to induce bubbles. The patient is then exposed to ultrasound which induces cavitation of the bubbles and generates heat in the vicinity of the nanoparticles.

SUMMARY OF THE INVENTION

The invention provides for a therapeutic apparatus for treating a subject and a computer program product comprising a set of executable instructions for execution by a therapeutic apparatus for treating the subject as claimed in the independent claims. Embodiments of the invention are given in the dependant claims.

A large static magnetic field is used by Magnetic Resonance Imaging (MRI) scanners to align the nuclear spins of atoms in order to produce images within the body of a subject. Induced gradients in the magnetic field and Radio Frequency (RF) electromagnetic waves are used to manipulate the orientation of the spins. This technique is also known as Magnetic Resonance (MR).

Computed Tomography (CT) is the construction of a three dimensional image of a patient using X-rays. High Intensity Focused Ultrasound (HIFU) is the use of focused ultrasound for the thermal or mechanical ablation of tumors.

Magnetic nanoparticles are nanoparticles that either have a permanent or an induced magnetic dipole moment. Magnetic nanoparticles can be heated in a subject through Brownian relaxation and also through Néel relaxation. In Brownian relaxation, heating is caused by changes in the physical orientation of the magnetic nanoparticle as the magnetic field is varied. In Néel relaxation, heating occurs not because the nanoparticle is spinning, but because orientation of the dipole moment is changing. In Néel relaxation the heating occurs within the nanoparticle and heat is transferred to the surrounding medium. Magnetic nanoparticles can be heated using a time varying magnetic field. The time varying magnetic field can be generated by coils. The time varying magnetic field can also be the magnetic portion of an electromagnetic field.

The concentration of magnetic nanoparticles in a subject can be detected using magnetic resonance imaging, because the magnetic particles can affect the orientation of the spins of protons adjacent to them. The concentration of magnetic nanoparticles can also be detected directly and measured quantitatively using Magnetic Particle Imaging (MPI). The magnetization of a magnetic particle is a function of the magnetic field applied to it. Beyond a threshold field strength, the magnetization of the magnetic particle saturates and a further increase in the magnitude of the magnetic field does not cause further magnetization. Magnetic Particle Imagine functions by using external magnetic fields and creating a region with a low magnetic field surrounded by regions of magnetic field that is sufficient to drive any magnetic particles into saturation. Any magnetic particles within the low field region will modulate an electromagnetic wave depending upon the concentration of the magnetic particles. In the saturated field region, the magnetic particles are already fully saturated and will not modulate the electromagnetic wave. Magnetic field gradient coils can be constructed to control the spatial location of the low field region. This technique can be used to construct three-dimensional images of the local concentration of magnetic nanoparticles within a subject.

The same effect used to image the local concentration of magnetic nanoparticles can also be used to selectively heat magnetic nanoparticles. In Focused Magnetic Particle Therapy (FMPT), magnetic field gradient coils are used to apply magnetic a magnetic field such that a region with a zero or low magnetic field is spatially surrounded by a region of a magnetic field sufficient to fully saturate any magnetic nanoparticles. A time varying magnetic field is then applied to the subject. The magnetic particles in the low field region are heated through Brownian and/or Néel relaxation, and the magnetic particles in the surrounding region are not heated.

Recently, the use of high intensity focused ultrasound for thermal ablation of tumors has received significant attention, especially in combination with magnetic resonance imaging as a means for temperature monitoring and effectively ensuring that the critical temperature for cell death is achieve in the target volume and that on the other hand, the ablated volume does not exceed the this volume by more than the desired margin (protection of risk organs). This approach is Food and Drug Administration-approved for the ablation of uterine fibroids and under consideration for the ablation of solid tumors in the liver, breast, prostate, and even the brain. However, its ability to focus is restricted by limitations of ultrasound penetration into the body: examples are lung nodules (air in the lungs stopping US penetration) and focal prostate lesions (pelvic bone preventing penetration from the front, forcing approaches through the rectum or the urethra with small transducers which have limited focusing ability. Also for large transducer arrays such as those used for uterine fibroids and considered for liver tumors, the focus is limited to a cigar-shaped volume of approximately 1.5 mm by 5 mm (the cigar pointing away from the transducer array).

The RF-excitation of nanoparticles can be used to locally heat tissue to induce cell death. Focusing approaches include the targeting of nanoparticles to tumor proteins and the application of focusing via suitably selective RF antennas. Both approaches suffer from the problem that unless the particles are directly injected into the tumor, i.e. with intravenous injection of the particles, their concentration in the tumor does not allow for the generation of sufficient heat to kill the tumor cells.

Even with direct injection, which is an invasive approach, it is desirable to apply the RF excitation highly focused. Such focusing can be achieved with a new approach called focused magnetic particle therapy, which uses magnetic gradient fields to create a very small spot in which the RF excitation can lead to particle heating. Particles in all other locations are in saturation and will thus not respond to the RF excitation. This method is related to a new imaging method called magnetic particle imaging. The so-called "field-free-point", which is the minimum focus achievable with this approach, can be made isotropic or spherical, with a diameter in the order of 1 mm. Depending on the protocol, heat diffusion can lead to a slight enlargement of this minimum ablation volume.

Embodiments of the invention may combine the superior heating capabilities of the high intensity focused ultrasound approach with the superior focusing capabilities of focused magnetic particle therapy, thus also removing the disadvantages of both, the focusing weaknesses of high intensity focused ultrasound and the lack of sufficient heat generation of focused magnetic particle therapy, which results from a low particle concentration.

In a hybrid system combination with magnetic resonance imaging, this latter modality can be used to image the three-dimensional temperature distribution, allowing to verify that on the one hand the temperature elevation by high intensity focused ultrasound is both sufficiently large for the local focused magnetic particle therapy "temperature boost" to exceed the cell death temperature and then on the other hand it is sufficiently limited for the healthy regions to experience only a reversible, non-damaging temperature increase. Magnetic resonance imaging can also monitor the temperature in the target volume, as it is further increased by focused magnetic particle therapy for local cell killing, thus allowing verification that the planned therapeutic effect is achieved. Furthermore, magnetic resonance imaging can be used for real-time imaging of the anatomy, thus allowing detecting and tracking tumor motion and deformation. This information can be used to adapt the focused magnetic particle therapy focus and to ensure that it stays focused on the proper part of the target. In one embodiment, the function of three-dimensional temperature monitoring and target imaging could also be achieved with an ultrasound system capable of measuring temperature changes.

In another embodiment, the system consists of extending the focused magnetic particle therapy part of the system into a complete magnetic particle imaging system. This allows imaging of the three-dimensional bio-distribution of the particles prior to the therapy delivery, as a basis for dose planning. In this context, the fact that magnetic particle imaging is inherently quantitative, i.e. directly measures the particle concentration, is an additional advantage.

In another embodiment, high intensity focused ultrasound is used for heating a large tissue volume which contains the lesion to be ablated up to a temperature just below the threshold of cell death. This only requires limited focusing capabilities, because the heating in the affected regions outside the target volume will be reversible, and no cell damage will occur in these regions. Focused magnetic particle therapy is then used simultaneously in order to elevate the temperature in a very precisely defined volume above this threshold, thus ablating a precisely defined target region. The complete target volume can now be ablated by moving the focused magnetic particle therapy focus over this volume in a sequential manner, thus ablating the target volume region by region, or for sufficiently high local particle concentrations it can be swept over the target volume, effectively heating the regions in an intermittent scheme, in which the complete target volume temperature is eventually raised above the threshold.

Embodiments of the invention may allow for thermally ablating tumors with:

unprecedented geometrical precision due to the fine focus of focused magnetic particle therapy real-time monitoring and verification of dose delivery via magnetic resonance temperature mapping, real-time target imaging and target motion and deformation detection, real-time feedback of this information into the electronic focus control, and direct quantification of three-dimensional nanoparticle bio-distribution for dose planning.

In contrast to other focal therapies like brachytherapy and proton beam therapy, embodiments of the present invention allow repeated therapy in case of tumor recurrence, thus allowing for a conservative treatment approach, which is important for cancer therapies such as that for prostate cancer.

Embodiments of the invention may be used for the therapy of all tumors which can be reached with ultrasound, even a beam of unfocused ultrasound.

Embodiments of the invention may have the following advantages for the treatment of prostate cancer:

ability to treat multiple small lesions distributed in a complex geometry, ability to treat tumors where high intensity focused ultrasound cannot be precisely focused (due to the restriction to trans-rectal or trans-urethral transducer arrays), ability to treat tumors located close to critical structures such as rectal and bladder wall, nerve bundle, the damaging of which of which would impair the of quality of life of the patient, and ability to repeatability treat reoccurrences of lesions, which if only monitored in a surveillance scheme, may turn aggressive one by one over time.

Embodiment of the invention may also be beneficial for the treatment of tumors of the lung (which appear as multiple, relatively small nodules) and of tumors close to the spinal cord as well as of intra-cranial tumors.

Embodiments of the invention provide for a therapeutic apparatus for treating a subject comprising a first heating means adapted for heating a first region of the subject, a first control means for controlling the power directed into the first region by the first heating means such that the power stays below a threshold value, and a particle heating means adapted for heating magnetic nanoparticles within a second region of the subject using a time-varying magnetic field. The first region comprises the second region.

This embodiment is advantageous, because hyperthermia can be an effective way to ablate tissue or to destroy tumors. Techniques such as high-intensity focused ultrasound have the disadvantage that they cannot be used adjacent to critical anatomical structures or near bone structures or in the lungs because it is difficult to properly direct and focus the ultrasound. This embodiment describes a first heating means which is used to raise the temperature of a first region of the subject to a higher temperature, but this temperature is not high enough to cause cell death.

The first region of the subject can be heated in a variety of different ways. Examples are the use of ultrasound, electromagnetic radiation, such as radio waves, infrared radiation, or microwaves. These techniques can all be used to heat bulk regions of the subject.

In various embodiments, the first control means can be implemented using a computer, a microcontroller, a microprocessor, an array of microprocessors, a digital electronic circuit, an analog electronic circuit, a mechanical regulator adapted for controlling a control signal, a switch, and/or a relay.

In an embodiment, the particle heating means comprises a magnet. In various embodiments, the magnet can comprise a superconducting magnet, a permanent magnet, an electromagnet, and/or separate coils for generating a magnetic field. In one embodiment, the particle heating means is combined into a magnetic resonance imaging system and at least a portion of the magnetic field used for magnetic resonance imaging is generated using an electromagnet. The electromagnet can ideally be turned off when magnetic resonance imaging data is not being acquired to make it easier to generate the low or zero magnetic field region necessary to perform magnetic particle imaging and/or focused magnetic particle imaging. In an embodiment of the invention, the particle heating means contains coils and power supplies to generate a magnetic field component with a gradient. This allows a region of low or zero magnetic field to be generated and its position to be controlled. In an embodiment the particle heating means comprises a radio frequency generator which generates a radio frequency electromagnetic field in the second region. The magnetic component of the radio frequency electromagnetic field heats the magnetic nanoparticles. In another embodiment a time varying magnetic field is generated in the second region using a coil and a power supply adapted for generating a time varying current. The time varying magnetic field in this embodiment heats the magnetic nanoparticles.

In an embodiment, the first heating means can be implemented as a High Intensity Focused Ultrasound unit (HIFU). In another embodiment, the first heating means is implemented as an ultrasound source that does not focus the ultrasound. In another embodiment the first heating means is has an antenna adapted for directing radio frequency radiation from a radio frequency generator towards the first region. In another embodiment, the first heating means is implemented as a microwave source that directs microwave energy towards the first region.

In another embodiment, the first heating means is implemented as an infrared light source which heats the tissue. Such an infrared source could be used to heat tissue during the treatment of breast tumors.

In another embodiment the threshold value is selected such that the temperature increase in the first region due to the ultrasonic heating means does not induce cell death. In addition, the second region comprises at least one hyperthermia zone which has a concentration of magnetic nanoparticles sufficient to cause a temperature increase which induces cell death when heated by the magnetic particle heating means.

This embodiment is advantageous, because it can be difficult to get a large concentration of magnetic nanoparticles in the vicinity of a tumor. The first heating means first raises the temperature of the hyperthermia zone and the surrounding tissue to a temperature which does not induce cell death, and then the particle heating means is used to additionally heat any magnetic nanoparticles within the second region. This causes a rise in the temperature in the hyperthermia zone which can then cause cell death.

In another embodiment the first heating means is adapted for heating the first region of a subject using one of the following: ultrasound, infrared radiation, electromagnetic radiation, radio waves, or microwaves. This is advantageous, because ultrasound, radio waves, or microwaves can all be used to heat relatively large volumes of a subject, or they can be used to heat a focused region of the subject. This offers a broader range of therapeutic choices for a physician.

In another embodiment the particle heating means modulates the magnetic field in the second zone such that it heats the magnetic nanoparticles using one of the following mechanisms: Brown relaxation, Néel relaxation, or a combination of Brown relaxation and Néel relaxation. In Brown relaxation, the physical orientation of the magnetic nanoparticle is changed. The change in the physical orientation of the nanoparticle is what heats it and the surrounding tissue or fluid around the particle. In Néel relaxation, the heating occurs not by changing the physical orientation of the particle but by changing the orientation of the magnetic moment of the particle. These two mechanisms are caused by a changing magnetic field, and the dominant mechanism depends upon the frequency of the changing magnetic field. There can also be a transition region where both Brown relaxation and Néel relaxation are used to heat the particle.

This embodiment is advantageous, because the changing magnetic field can be spatially controlled and can be used to precisely heat the desired nanoparticles.

In another embodiment the ultrasonic heating means is a high-intensity focused ultrasound unit. This embodiment is advantageous, because high-intensity focused ultrasound can be used to relatively precisely ablate tissue. The ultrasonic transducer of the high-intensity focused ultrasound unit can be designed to either give a sharp focus and ablate tissue directly or it can be designed to heat a larger region that is still relatively focused. This embodiment is advantageous also because this unit can be designed to heat an area such as the prostrate.

In another embodiment the particle heating means further comprises a magnetic field generation means adapted for heating the magnetic nanoparticles using focused magnetic particle therapy. The apparatus further comprises a second control means for controlling the particle heating means and is adapted for controlling the location of the second region. The second control means is adapted to receive planning data for planning treatment of the subject, and the therapeutic apparatus is adapted for performing therapy using the planning data. The second and first control means can be implemented using a single control means. The second control means can be implemented using a computer, a microcontroller, a microprocessor, an array of microprocessors, a digital electronic circuit, and an analog electronic circuit. The second control means and/or the first control means can comprise a computer program product.

This embodiment is advantageous, because focused magnetic particle therapy can be used to heat magnetic nanoparticles in a very precisely defined volume. This allows very precise control which magnetic nanoparticles are heated. The therapy could be planned by a physician using a medical scanner such as a 3D X-Ray system, a CT system, a positron emission tomography system, a Single Photon Emission Computed Tomography scanner, a 3D ultrasound imaging system or a magnetic resonance imaging system to provide images of the anatomy and plan the therapy session. The second control means is then adapted to receive this planning data and perform the therapy using this planning data.

In an embodiment, the magnetic field generation means comprises a magnet. In various embodiments, the magnet can comprise a superconducting magnet, a permanent magnet, an electromagnet, and/or coils for generating a magnetic field. In one embodiment, the particle heating means is combined into a magnetic resonance imaging system and at least a portion of the magnetic field used for magnetic resonance imaging is generated using an electromagnet. The electromagnet can ideally be turned off when magnetic resonance imaging data is not being acquired to make it easier to generate the low or zero magnetic field region necessary to perform magnetic particle imaging and/or focused magnetic particle imaging.

In another embodiment the magnetic field generation means is further adapted for acquiring medical image data within an imaging zone using magnetic particle imaging. The imaging zone comprises the first region and the second control means is adapted for generating planning data using the medical image data.

This embodiment is advantageous, because magnetic particle imaging allows the very precise determination of the quantitative local distribution of magnetic nanoparticles within a subject. The knowledge of the quantitative local distribution of the magnetic nanoparticles relative to the anatomy of the subject is useful in planning therapy. Anatomical data can be acquired using an MRI scanner, a positron emission tomography scanner, a Single Photon Emission Computed Tomography scanner, a 3D X-Ray imaging system, a 3D ultrasound imaging system or a computer tomography scanner and then compared with the medical image data obtained from the magnetic particle imaging.

In another embodiment the therapeutic apparatus further comprises a magnetic resonance imaging system adapted for acquiring medical image data within an imaging zone. The imaging zone comprises the first region and the second control means is adapted for generating planning data using medical image data. This embodiment is advantageous, because magnetic resonance imaging data contains useful anatomical information for planning the treatment of a subject. Magnetic resonance imaging gives very detailed anatomical information and magnetic particle imaging gives very detailed information on a local distribution of magnetic nanoparticles within a subject. These two imaging modalities are therefore very complimentary for planning the treatment of a subject.

In another embodiment the magnetic resonance imaging system is adapted for acquiring temperature data using magnetic resonance thermometry. The medical image data comprises temperature data and the first control unit is adapted for limiting the temperature in the first region using the medical image data. The second control unit is adapted for controlling the temperature in the second region using the medical image data. This embodiment is advantageous, because magnetic resonance thermometry can be used to make detailed real time measurements of the temperature within a subject. This can be used to very precisely control the treatment of the subject.

In another embodiment the therapeutic apparatus is adapted for acquiring medical image data at periodic intervals. The therapeutic apparatus is adapted for identifying the location of a target region within the subject using the medical image data. The target region can be identified using well-known image segmentation techniques. The second control means is adapted for generating real time planning data using the location and shape of the target region. This can be implemented using organ shape and deformation models implemented in software. Such models can be trained such that they are able to adjust location of a second region based upon the motion and/or deformation of the complete organ or a target region thereof, using the real time planning data. This embodiment has the advantage that the therapeutic apparatus can be used to account for the changes occurring when the subject moves. This leads to a more accurate and precise control of the therapeutic apparatus.

In another embodiment the therapeutic apparatus is operable for treating any one of the following: tumors in an eye, tumors in the brain, tumors in nerve bundles, tumors in the spinal cord, tumors in the lung, tumors in the prostate gland, tumors adjacent to an eye, tumors adjacent to the brain, tumors adjacent to nerve bundles, tumors adjacent to a lung, tumors adjacent to the prostate gland, tumors adjacent to the walls of the bladder, tumors adjacent to the rectum, tumors adjacent to an organ boundary, multiple tumors distributed throughout the subject, tumors with multiple small foci, tumors adjacent to the heart, tumors adjacent to air tissue boundaries, or tumors adjacent to bone tissue boundaries.

This embodiment is advantageous, because in all of these cases it would be difficult to treat these with high-intensity focused ultrasound or other techniques, because the therapy needs to be very precisely directed into the patient to avoid injuring an organ or a structure next to an organ.

In another aspect the invention provides for a computer program product comprising a set of executable instructions for execution by a therapeutic apparatus for treating a subject. The set of executable instructions comprise the steps of: controlling a first heating means adapted for heating a first region of a subject such that a power directed into the first region by the first heating means stays below a threshold value, and controlling a particle heating means adapted for heating magnetic nanoparticles within a second region using a time-varying magnetic field. The first region comprises the second region.

An advantage of this embodiment is that implementing the control of a therapeutic apparatus using a computer program product enables the therapeutic apparatus to function more rapidly and efficiently than if a human operator was using it. Other advantages of this embodiment have been previously described.

In another embodiment the therapeutic apparatus for treating a subject has a particle heating means that comprises a magnetic field generation means adapted for focused magnetic particle therapy. The computer program product further comprises the steps of: receiving planning data for planning treatment of the subject, controlling the treatment of the subject using the planning data, and controlling the location of the second region using the magnetic field generation means. The benefits of this embodiment have been previously discussed.

In another embodiment the computer program product further comprises the steps of: acquiring medical image data within an imaging zone using magnetic particle imaging and/or magnetic resonance imaging, and generating planning data using the medical image data. The imaging zone comprises the first region. The advantages of this embodiment have been previously discussed.

In another embodiment the computer program product further comprises the steps of acquiring medical image data at periodic intervals, identifying the location and shape of a target region within a subject using the medical image data acquired at periodic intervals, generating real time planning data using the location and shape of the target region, and adjusting location of the second region based upon motion and/or deformation of the target region using the real time planning data. Advantages of this embodiment have been previously discussed.

DESCRIPTION OF THE DRAWINGS

In the following preferred embodiments of the invention will be described, by way of example only, and with reference to the drawings in which.

DETAILED DESCRIPTION

Figure 1:
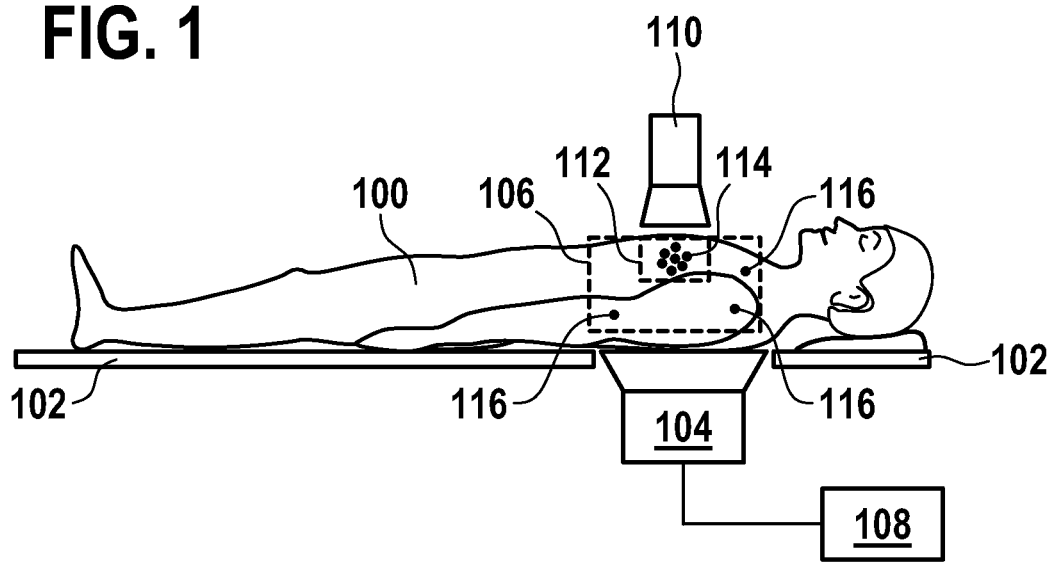
FIG. 1 shows a functional diagram of an embodiment of a therapeutic apparatus according to the invention.
Figure 2:
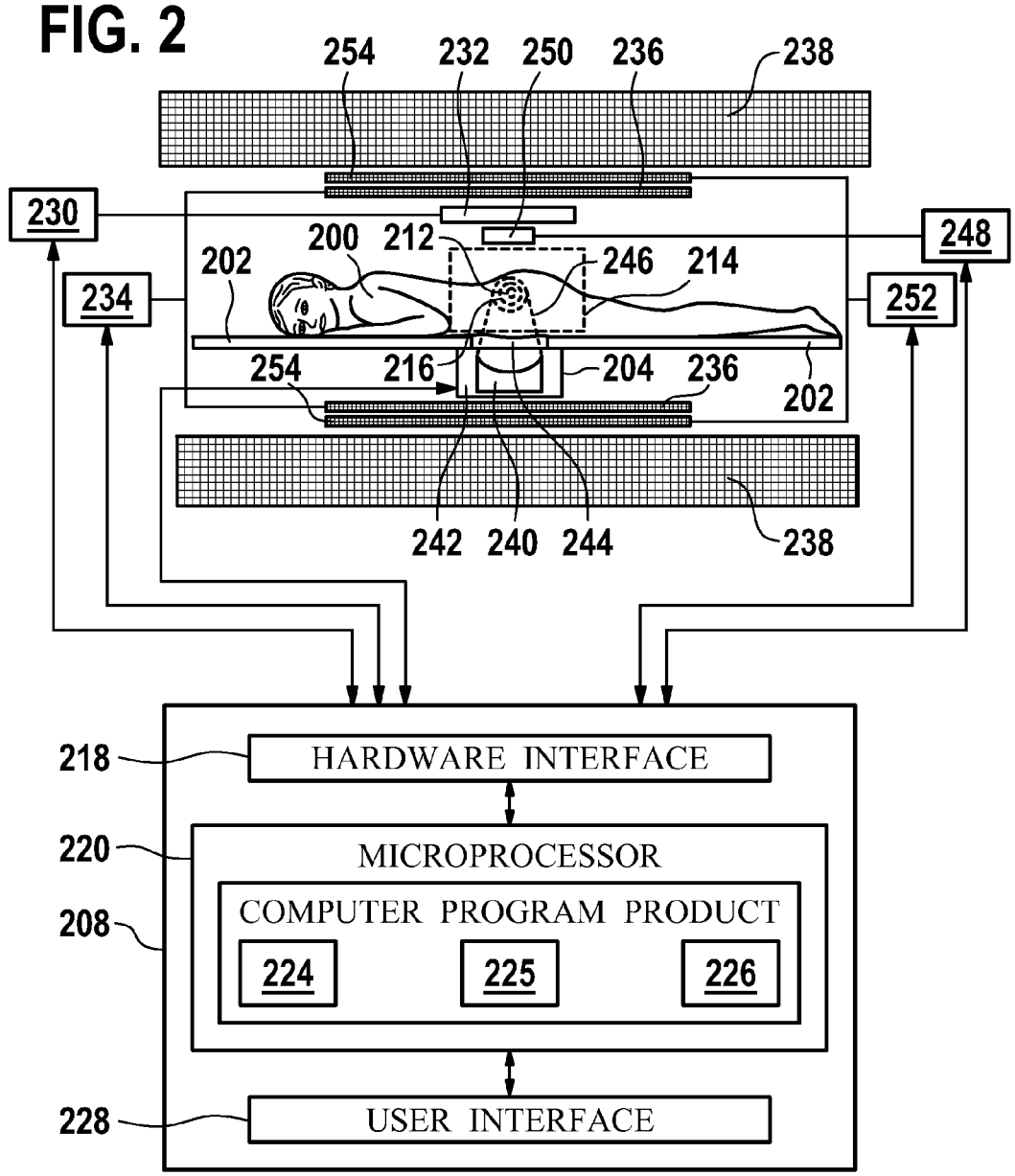
FIG. 2 shows a functional diagram of an alternative embodiment of a therapeutic apparatus according to the invention.
Figure 5:
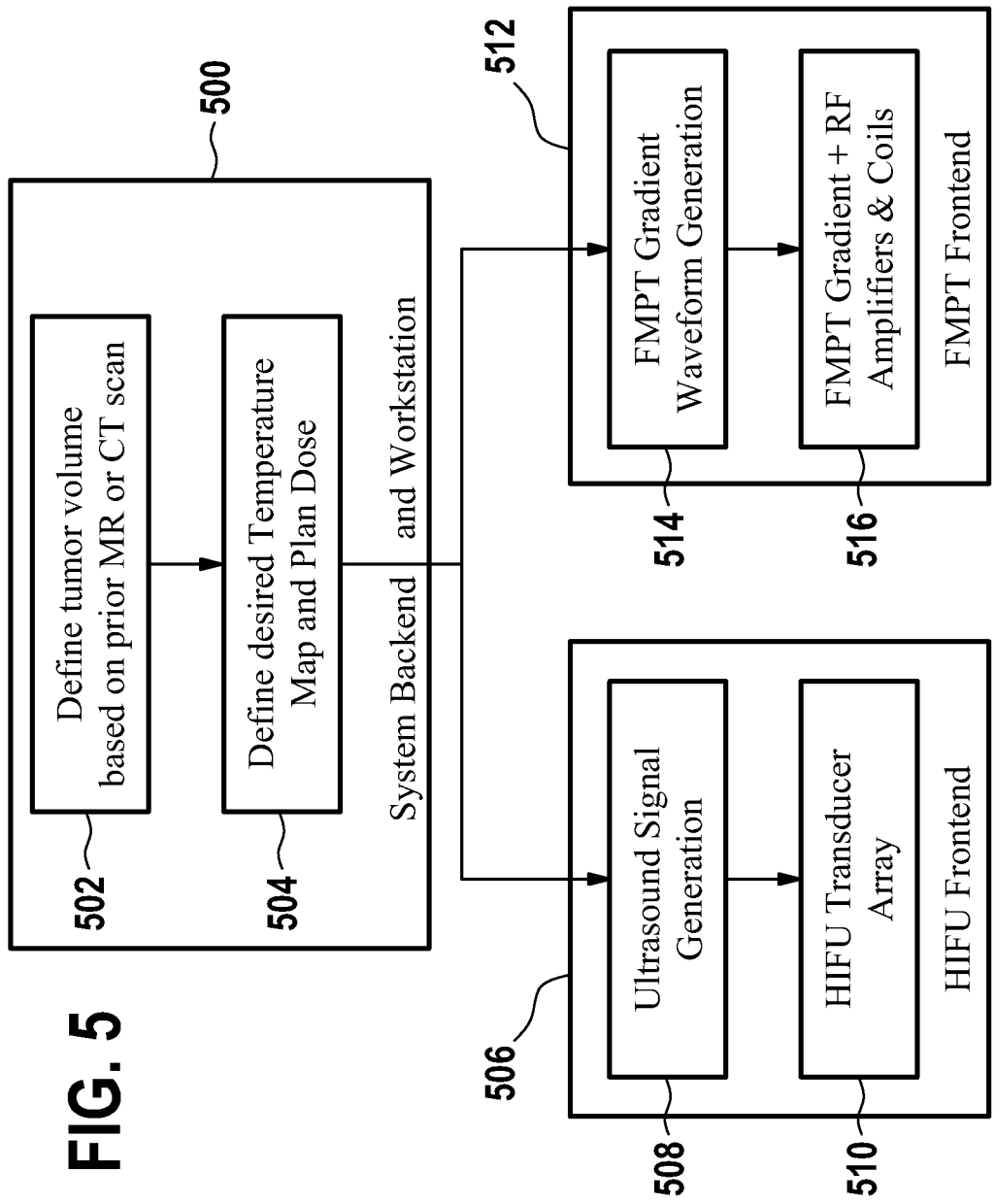
FIG. 5 shows a block diagram of an embodiment of a therapeutic apparatus according to the invention.
Figure 6:
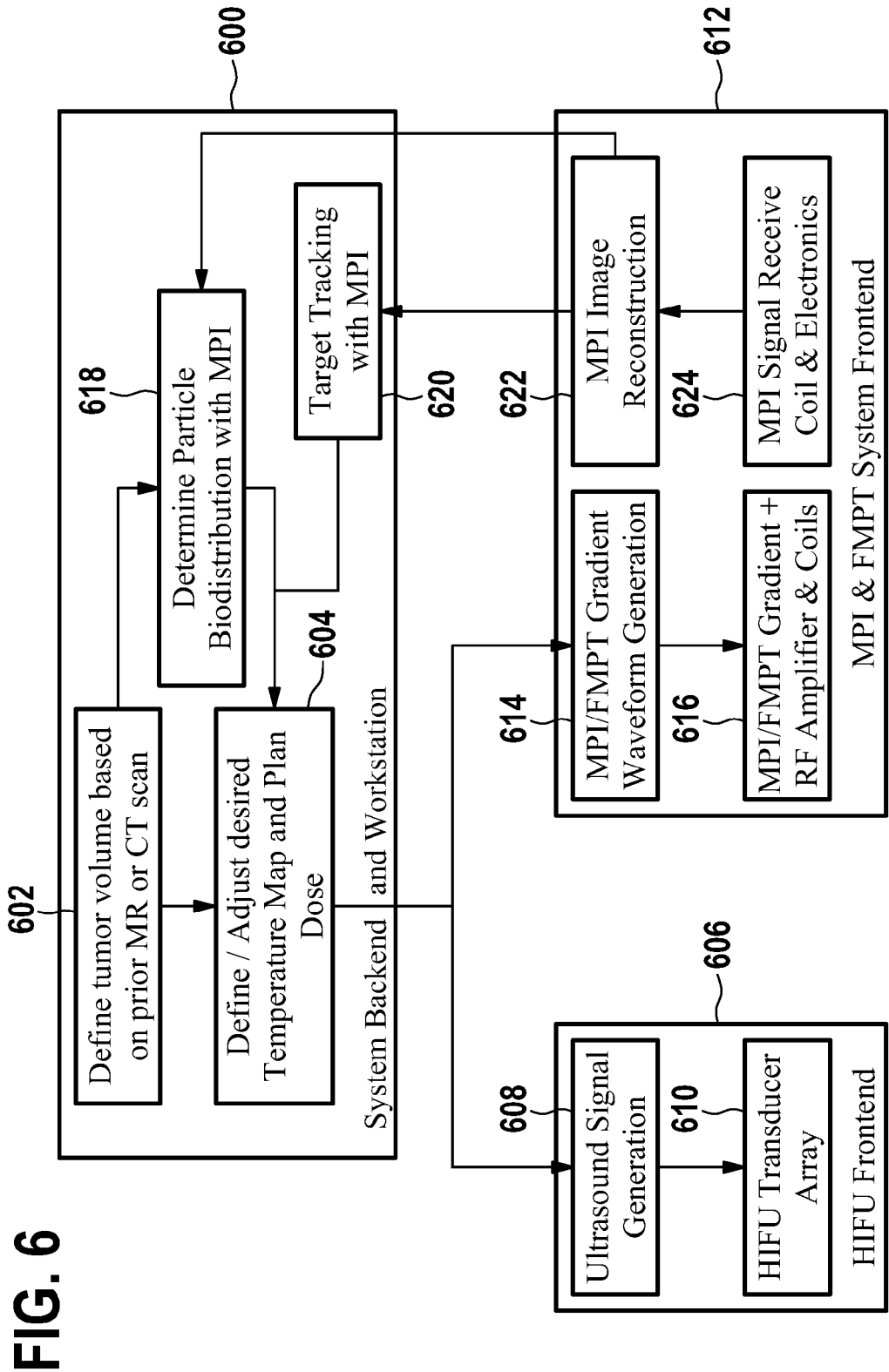
FIG. 6 shows a block diagram of an alternative embodiment of a therapeutic apparatus according to the invention.
Figure 7:
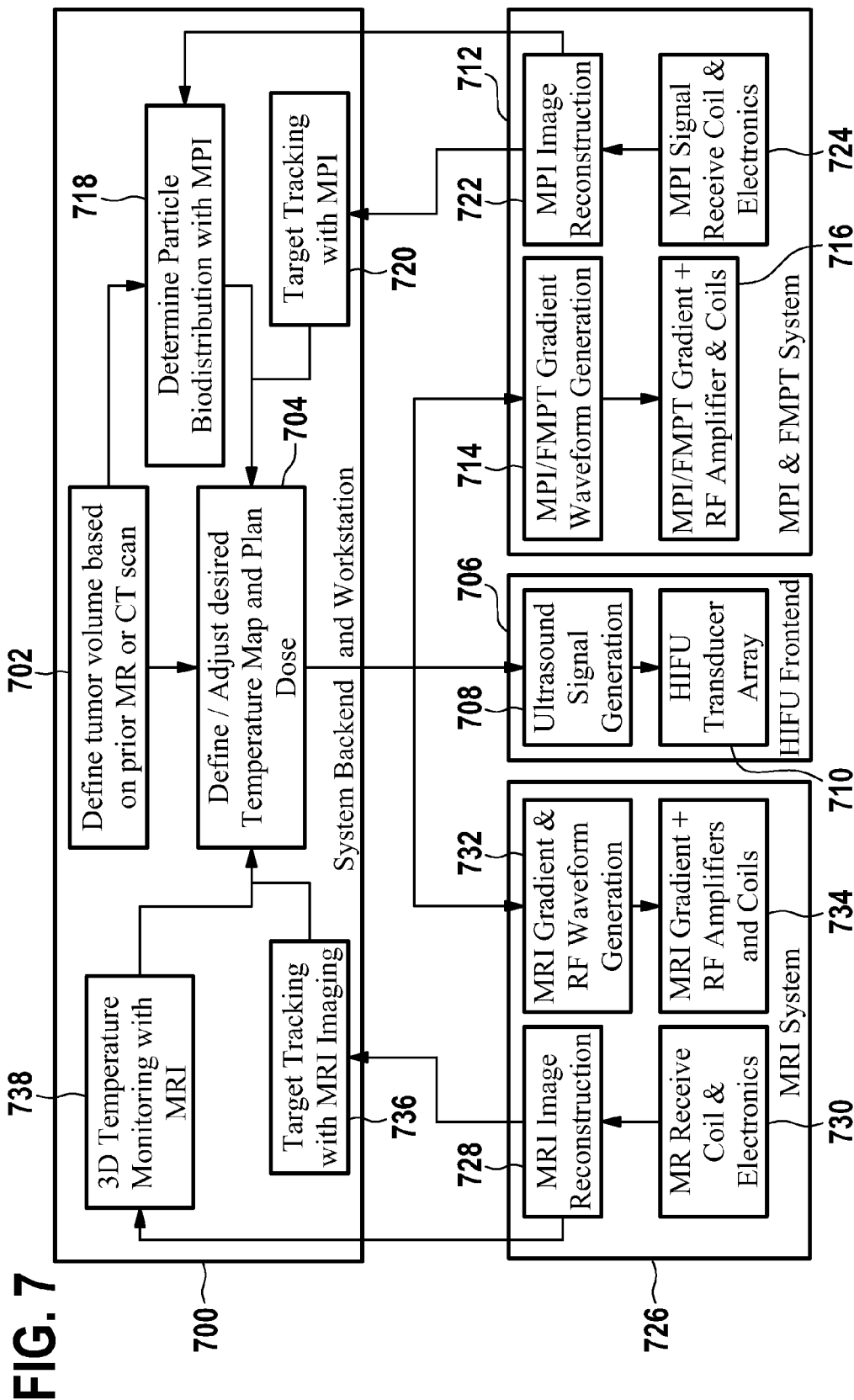
FIG. 7 shows a block diagram of an alternative embodiment of a therapeutic apparatus according to the invention.

In FIG. 1 and FIG. 2, the numbering of elements is chosen such if that the two least significant digits of the numbering match then the element in FIG. 1 and FIG. 2 are either identical or perform the same function. In FIG. 5 through FIG. 7, the numbering of elements is chosen such if that the two least significant digits of the numbering match then the element in FIG. 5 through FIG. 7 are either identical or perform the same function. Elements which have been discussed previously will not necessarily be discussed in description of later figures if the elements are identical or perform the same function.

FIG. 1 shows a functional diagram of an embodiment of a therapeutic apparatus. A subject 100 is resting on a subject support 102. There is a first heating means 104 which is used for heating a first region 106 of the subject 100. There is a first control means 108 that controls the first heating means 104 such that the temperature of the first region 106 stays below a threshold. There is a particle heating means 110 which heats magnetic nanoparticles within the second region 114. The second region 112 is the area in which the particle heating means 110 is able to heat the magnetic nanoparticles. In this figure it is also visible that there are magnetic nanoparticles 116 that are not within the second region. These magnetic nanoparticles are not heated by the particle heating means. This figure demonstrates how the combination of the first heating means 104 and the particle heating means 110 can be used to precisely heat and treat a subject 100. The first heating means can be implemented using a variety of methods, such as high-intensity focused ultrasound, microwave radiation or radio frequency radiation. The particle heating means can be used to heat particles using a changing magnetic field or a radio frequency field.

FIG. 2 shows another embodiment of a therapeutic apparatus according to the invention. This figure is also a functional diagram. The embodiment shown in this figure incorporates high-intensity focused ultrasound, magnetic resonance imaging, magnetic particle imaging, and focused magnetic particle therapy. In this embodiment there is a subject 200 resting on a subject support 202. There is a high-intensity focused ultrasound unit 204 which directs ultrasound into the subject 200. The high-intensity focused ultrasound unit 204 comprises a volume filled with a medium that conducts ultrasound 242 and inside of this is an ultrasound transducer 240 which is used to generate and focus the ultrasound 246. Located within the patient support 202 is an adapter for receiving an ultrasound coupling medium 244. The ultrasound coupling medium occupies a space between the high-intensity focused ultrasound unit 204 and the subject 200. The ultrasound coupling medium can be water, it can be an ultrasound coupling gel or it can be an ultrasound coupling gel pad. The ultrasound transducer 240 can be designed such that the ultrasound is directed to a small point or it can be designed such that the ultrasound is directed into a volume. In this example the ultrasound is directed into the first region 206.

The apparatus further comprises a magnetic field generation means 238. This is used to generate the large magnetic fields that are used for magnetic resonance imaging, magnetic particle imaging, and/or the focused magnetic particle therapy. This can be a superconducting magnet or it can be an electromagnet. It can also contain elements consisting of permanent magnets. There are magnetic resonance imaging gradient coils 236 for creating the magnetic field gradients during magnetic resonance imaging. The magnetic resonance imaging gradient coils 236 are connected to a magnetic field gradient power supply 234. The magnetic field gradient power supply is adapted for supplying current to the magnetic resonance imaging gradient coils 236 for producing gradients in the magnetic field.

There is also a magnetic resonance imaging transceiver coil 232 which is used for the excitation of nuclei during magnetic resonance imaging. The magnetic resonance imaging transceiver coil 232 is connected to a magnetic resonance imaging radio frequency transceiver 230. The magnetic resonance imaging radio frequency transceiver 230 is adapted for transmitting the radio frequency pulses to the magnetic resonance imaging transceiver coil 232 necessary to excite nuclei during magnetic resonance imaging. The magnetic resonance imaging transceiver coil 232 and transceiver 230 are adapted for receiving the radio frequency signals emitted as the excited nuclei relax. These radio frequency signals are defined herein as magnetic resonance imaging data.

There is also a magnetic particle imaging and/or focused magnetic particle therapy magnetic field gradient coil 254 for creating the magnetic field gradients necessary for performing magnetic particle imaging or focused magnetic particle therapy. This magnetic particle imaging and/or focused magnetic particle therapy magnetic field gradient coil 254 can be geometrically located outside of, or inside of, or co-planar with the magnetic resonance imaging gradient coils 236. FIG. 2 shows the magnetic particle imaging and/or focused magnetic particle therapy magnetic field gradient coil 254 located at a larger radius or outside of the magnetic resonance imaging gradient coils 236. The magnetic particle imaging and/or focused magnetic particle therapy magnetic field gradient coil 254 generates a magnetic field using current supplied by a magnetic particle imaging and/or focused magnetic particle therapy magnetic field gradient coil power supply 252. The particle imaging and/or focused magnetic particle therapy magnetic field gradient coil in this embodiment 254 are adapted such that they are able to effectively counteract the magnetic field of the magnetic field generation means 238. Both magnetic particle imaging and focused magnetic particle therapy rely on the ability to cancel out the total sum of all static and gradient magnetic fields in a small volume. In some embodiments, the magnetic field gradient coil 254 is strong enough to counteract the magnetic field of the magnetic field generating means 238. In some embodiments the magnetic field generating means 238 comprises an electromagnet which can be turned off during magnetic particle imaging and/or focused magnetic particle therapy and turned on during magnetic resonance imaging.

In some embodiments the magnetic resonance imaging magnetic field coil power supply can be integrated with the magnetic particle imaging and/or focused magnetic particle therapy magnetic field coil power supply; and the magnetic resonance imaging magnetic field coil can be integrated with the magnetic particle imaging and/or focused magnetic particle therapy magnetic field coil. This integration can take the form of the two coils being interlaced and being incorporated into a single design element or the same magnetic field gradient coil can be used for magnetic resonance imaging, magnetic particle imaging, and/or focused magnetic particle therapy.

The magnetic resonance imaging radio frequency transceiver 230, the high-intensity focused ultrasound unit 204, the magnetic resonance imaging magnetic field gradient power supply 234, the magnetic particle imaging and/or focused magnetic particle imaging radio frequency transceiver, and the magnetic particle imaging and/or focused magnetic particle imaging gradient power supply are connected to the hardware interface 218 of a computer system 208. The computer system 208 is used to control the therapeutic apparatus during its therapy. The computer system 208 comprises the hardware interface 218, a microprocessor 220, and a user interface 228. The hardware interface 218 is used for controlling the system. The microprocessor 220 is adapted for executing a computer program product 222 which is adapted for controlling the therapeutic apparatus. In some embodiments the microprocessor 220 is an array of microprocessors. In some embodiments, the computer system 208 performs image processing and image reconstruction on the magnetic resonance imaging data. The computer program product 222 comprises a target zone identification module 224, a planning data generation module 226, and a target motion and computation module 225. The target zone identification module 224 can be implemented using standard image segmentation techniques and is used to identify the region of the patient to be treated. This can be done either in real time or it can be assumed that the patient remains motionless during the treatment.

The planning data generation module 226 and the target motion module 225 can be implemented using pattern recognition algorithms. In some embodiments the target motion module identifies the motion of the subject's 200 anatomy and uses this information to predict the position and shape of the target zone 216. The prediction of the location and position of the target zone helps to improve the accuracy of the heating of the target zone when the patient or a portion of the patient is in motion.

In an embodiment, the planning data generation module 226 is implemented as trained pattern recognition module. This has the advantage that the pattern recognition module can be trained using a set of training images, where the volume or volumes of interest have been correctly placed. This could be implemented by using a variety of different methods. Examples of different methods or algorithms that could be used are: Principal Component Analysis, Neural Network, CN2 algorithm, C4.5 algorithm, Iterative Dichotomiser 3 (ID3), nearest neighbor search algorithm, naive Bayes classifier algorithm, Holographic Associative Memory, or perception learning algorithm.

In an embodiment, the target motion and computation module 225 is implemented as trained pattern recognition module. This has the advantage that the pattern recognition module can be trained using a set of training images, where the volume or volumes of interest have been correctly placed. This could be implemented by using a variety of different methods. Examples of different methods or algorithms that could be used are: Principal Component Analysis, Neural Network, CN2 algorithm, C4.5 algorithm, Iterative Dichotomiser 3 (ID3), nearest neighbor search algorithm, naive Bayes classifier algorithm, Holographic Associative Memory, or perception learning algorithm.

The planning data generation module 226 uses the data from the target zone identification module 224 to plan the treatment of the subject 200.

The image data is acquired in imaging zone 214. The ultrasound has been focused to a region known as the first region 206. Within the first region the region 212 is identified. The target zone 216 is identified and then the therapy is planned to control the location of the second region 212 such that the entire target zone 216 is treated. In this example the target zone 216 is larger than the second region 212. During the course of therapy the second region 212 is moved such that the entire target zone 216 is treated.

Figure 3:
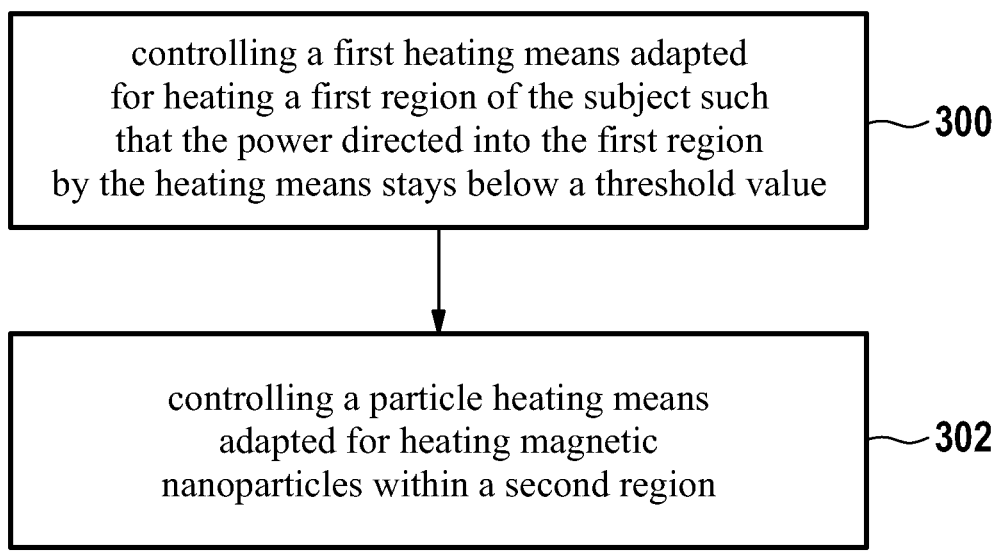
FIG. 3 shows a flow diagram of an embodiment of machine executable steps for controlling a therapeutic apparatus according to the invention.

FIG. 3 shows a flow diagram of an embodiment of machine executable steps for controlling a therapeutic apparatus according to the invention. In step 300 a first heating means is controlled such that a first region of the subject is heated such that the power directed into the first region by the heating means stays below a threshold value. Step 302 is controlling a particle heating means adapted for heating magnetic nanoparticles within a second region. In the simplest embodiments of the invention, complex medical imaging and targeting is not necessary to precisely deliver the intended temperature increase to the target zone. Limiting the power delivered to the first region has the effect of limiting the temperature increase caused by the first heating means. In more complicated embodiments a means for measuring the temperature within the first region can be used to actively control the power delivered to the first region to precisely control the temperature increase within the first region caused by the first heating means.

Figure 4:
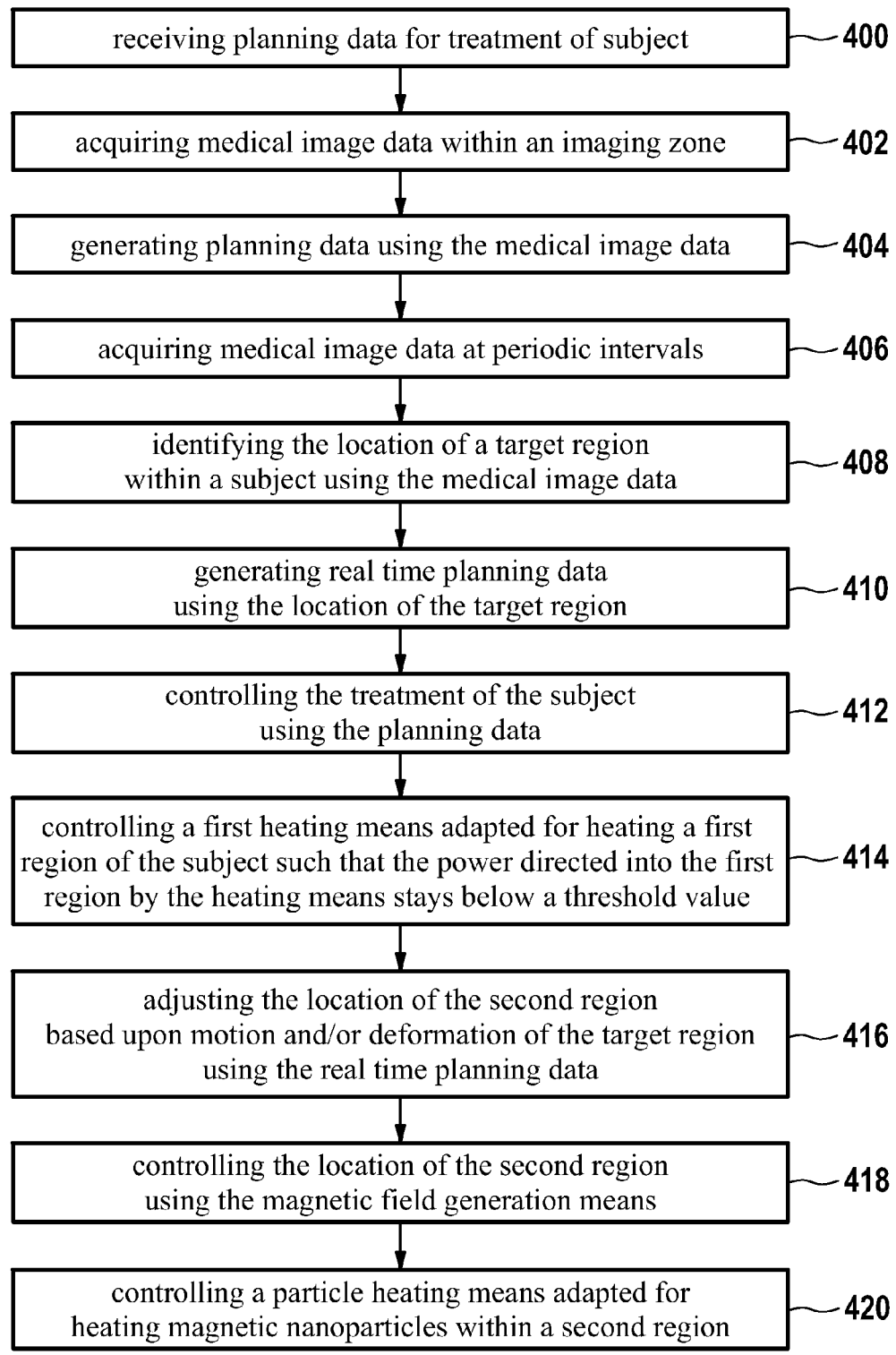
FIG. 4 shows a flow diagram of an alternative embodiment of machine executable steps for controlling a therapeutic apparatus according to the invention.

FIG. 4 shows a flow diagram of an embodiment of machine executable steps for controlling a therapeutic apparatus according to the invention. Step 400 is receiving planning data for treatment of a subject. A physician can plan the therapy using a modality or combination of modalities such as magnetic resonance imaging, positron emission tomography, Single Photon Emission Computed Tomography, X-Ray imaging, computed tomography, or ultrasound. This medical imaging data can be used to develop a treatment and therapy plan for a subject.

The subject is then placed into the therapeutic apparatus and in step 402 is acquiring medical image data within an imaging zone. The therapeutic apparatus is useful to acquire medical imaging data to see if the treatment therapy plan is correct or appropriate. In step 404 it is generating planning data using the medical image data. In this step the received planning data is reconciled with the acquired medical image data. Next in step 406 is acquiring medical image data at periodic intervals. The subject can move externally or internally and cause the target zone of the patient to change. For this reason in step 408, location of the target zone region within a subject using the medical image data is identified. Next in step 410 real time planning data using a location of the target region is generated. In step 412 the treatment of the subject using the planning data is then controlled. The controlling of the treatment of the subject using the planning data is performed in steps 414, 416, 418, and 420.

Step 414 is controlling a first heating means adapted for heating a first region of the subject such that the power directed into the first region by the heating means stays below a threshold value. Step 416 is adjusting the location of the second region based upon motion and/or deformation of the target region using the real time planning data. Step 418 is controlling the location of the second region using the magnetic field generation means and step 420 is controlling the particle heating means adapted for heating magnetic nanoparticles within a second region.

FIG. 5 shows a block diagram of an embodiment of a therapeutic apparatus according to the invention. The embodiment shown in FIG. 5 comprises three different systems. It comprises the system backend and workstation 500, the high intensity focused ultrasound frontend 506, and the focused magnetic particle therapy frontend 512.

The system backend and workstation 500 is the computer and control system of the therapeutic apparatus. It comprises elements 502 for defining the tumor volume based on a prior magnetic resonance or computed tomography scan. The tumor volume defined by element 502 is used by element 504 for defining a desired temperature map and to plan the dose distribution. The planning data generated by element 504 is used by both the high intensity focused ultrasound frontend 506 and the focused magnetic particle therapy frontend 512.

The high intensity focused ultrasound frontend comprises elements which generate an ultrasound signal 508 and the high-intensity focused ultrasound transducer assembly 510 which is used to generate the ultrasound. The focused magnetic particle therapy frontend comprises element 514 for generating a focused magnetic particle therapy gradient waveform generation. This waveform is then used by the focused magnetic particle therapy gradient and radio frequency amplifiers and coils 516 to perform the focused magnetic particle therapy.

The embodiment of the invention is shown in FIG. 5 has a workstation with software for the therapy planning and system control (backend) 500, where the clinician defines the tumor volume and target volume using element 502 based on prior three-dimensional imaging information from 3D X-Ray imaging, 3D Ultrasound imaging, magnetic resonance imaging or computed tomography. Based on this, a desired temperature map/heat dose plan is defined by element 504, which is the basis for thermal ablation. This is translated into the generation of the ultrasound signal in the high intensity focused ultrasound frontend 506, which is then applied to heat the region around the tumor, and into the generation of the focused magnetic particle therapy gradient waveform required to create the fine focus covering the target region, in which the RF excitation of the focused magnetic particle therapy system elevates the temperature above the critical value for cell death.

Since ultrasound transducer arrays 510 are compatible with strong gradient field switching, as has been proven by current magnetic resonance guided high intensity focused ultrasound systems, a simple embodiment could be a similar configuration. This possible embodiment has a tubular gradient system to create the focused magnetic particle therapy focus, and a high intensity focused ultrasound transducer array for the temperature elevation in the larger region including the target. The RF coils for the excitation of the magnetic nanoparticles can be arranged inside the same assembly as the magnetic resonance imaging gradient coils, much like the transmit coils in current magnetic resonance imaging systems. For cylindrical bore magnets, the magnetic resonance imaging gradient coils are typically embedded within a cylinder. The RF coil for the excitation of magnetic nanoparticles and/or the magnetic resonance imaging transmit coils can be imbedded within the cylinder also.

FIG. 6 shows a block diagram of an embodiment of the therapeutic apparatus according to the invention. This embodiment is similar to the embodiment shown in FIG. 5 except that magnetic particle imaging components have been added to the system. There is now a feedback loop between the frontend for performing magnetic particle imaging and focused magnetic particle therapy 612 and the system backend and workstation 600. The focused magnetic particle therapy system frontend 512 of the embodiment shown in FIG. 5 has been modified to become a magnetic particle imaging and focused magnetic particle therapy system frontend 612.

This frontend 612 comprises several additional components over that shown in the embodiment of FIG. 5. There is now a magnetic particle imaging signal receive coil and electronics component 624 and the signals received by the coil are then used by element 622 which performs magnetic particle image reconstruction. The data concerning the reconstructed image is then fed back into the system backend and workstation 600. The data from element 622 is fed into element 620, which performs target tracking based on the MPI image data from element 622 and also into element 618, which determines the nanoparticle bio-distribution based on the MPI image data from element 622. Element 618 determines the bio-distribution and receives data from element 602 in which the defined tumor volume is defined based on a prior 3D X-ray, Ultrasound, magnetic resonance or computed tomography imaging information. Information from determination element 618 and element 620 are both fed into element 604, which defined and adjusts the desired temperature map or heat dose plan.

The embodiment shown in FIG. 6 is able to use the magnetic particle imaging data in conjunction with the previously acquired magnetic resonance, 3D X-ray, Ultrasound or computed tomography scan data. This is able to locate/register the location of the magnetic particle imaging volume in the coordinate system of these imaging scan data. This allows the distribution of particles to be determined relative to the anatomy of the subject. Once this is known this can be combined with real time motion tracking and deformation analysis of the 3D bio-distribution of magnetic particles within the subject, in order to precisely define and adjust a time dependant treatment plan.

The embodiment shown in FIG. 6, expands the focused magnetic particle therapy system 512 of FIG. 5 into a full magnetic particle imaging and therapy system 612. This involves adding additional magnetic particle imaging system components required for imaging: an RF receive coil configuration with suitable signal amplification and digitization and an image reconstruction unit. The resulting three-dimensional images can then be used for both the computation of the three-dimensional bio-distribution of the particles as an input to the dose planning unit, and for the position verification, motion tracking and deformation analysis of the target. The field gradient and RF excitation units can be largely identical for both magnetic particle imaging and focused magnetic particle therapy operation purposes. Since they need to be more flexible, they are thus shared between imaging and thermal ablation operation, which would be applied in an interleaved manner (heat-track-heat-track) during the therapy session. A suitable system configuration would be similar to the basic system; to which one or more RF receive coils for magnetic particle imaging would be added in a location as close as possible to the location of the tumor.

FIG. 7 shows a block diagram of an embodiment of a therapeutic apparatus according to the invention. The embodiment shown in FIG. 7 is a refinement of the embodiment shown in FIG. 6. The embodiment shown in FIG. 7 includes all the elements of the embodiment shown in FIG. 6 except that a magnetic resonance imaging system has also been included into the system. The system backend and workstation 700 includes several more elements and there is an additional magnetic resonance imaging system element 726. The magnetic resonance imaging system 726 comprises element 732 for generating a magnetic resonance imaging gradient and radio frequency waveform. Element 732 receives planning data from element 704, which defines and adjusts the temperature map or dose plan. Element 732 is used to control element 734. Element 734 comprises the magnetic resonance imaging gradient plus radio frequency amplifiers and coils. Element 734 is used to put the volume of the subject in a state where magnetic resonance imaging data can be received. Element 730 comprises a magnetic resonance receive coil and electronics. Element 730 receives the magnetic resonance imaging data and feeds them to element 728. Element 728 reconstructs magnetic resonance images from the magnetic resonance imaging data. The system backend and workstation 700 comprises a module element 736 for motion detection and target tracking with magnetic resonance imaging and an element 738 for three-dimensional temperature monitoring based on magnetic resonance thermometric imaging. Both of these elements receive the reconstructed MRI data from the magnetic resonance imaging reconstruction element 728. Both elements 736 and 738 can be implemented as software modules. Magnetic resonance imaging allows the detection of the complete motion of the anatomy, not only in the target region. The detection of the overall motion allows the derivation of a motion prediction for the target. Element 736 can be adapted to predict the motion of the target region, which aids in accurately determining the new target position and any deformation of the target region resulting from the overall motion of the anatomy.

Elements 738 and 736 are both used by element 704 to initially plan and later adjust (based on new information about the target location and deformation) the therapy of the subject. In this embodiment, the information obtained from element 736 allows to detect and quantify motion in the complete MRI imaging volume, based on the excellent anatomical contrast of MRI. In the temperature map/dose plan definition and adjustment element 704, this motion information is combined with the information about the changed bio-distribution of the magnetic nanoparticles from element 720. This combination allows for a more accurate analysis of motion and deformation of the target volume than is possible from the magnetic particle imaging information alone.

The embodiment in FIG. 7 has been augmented with a magnetic resonance imaging system for three-dimensional temperature monitoring during the treatment and for improved target position verification, motion tracking and deformation analysis. The measured three-dimensional temperature distribution is fed into the dose planning unit of the system for potential adjustments if the measured temperature distribution deviates from the planned one. Likewise, both the three-dimensional MRI image of the patient and the MPI image of the target can be used to adjust the focused magnetic particle therapy focus in case the target has moved or deformed (due to patient motion). This magnetic resonance imaging-based target imaging will be greatly enhanced as compared to the target imaging based on magnetic particle imaging, because magnetic resonance imaging images will show the full anatomy, versus magnetic particle imaging just shows the particle distribution (relying on an accumulation of particles in the tumor to indicate its location).

LIST OF REFERENCE NUMERALS

100 Subject
102 Subject support
104 First heating means
106 First region
108 First control means
110 Particle heating means
112 Second region
114 Magnetic nanoparticles within second region
116 Magnetic nanoparticles not within second region
200 Subject
202 Subject support
204 High intensity focused ultrasound unit
206 First region
208 Computer
212 Second region
214 Imaging zone
216 Target zone
218 Hardware interface
220 Microprocessor
222 Computer program product
224 Target zone identification module
225 Target motion and computation module
226 Planning data generation module
228 User interface
230 Radio Frequency transceiver
232 Transceiver coil
234 Magnetic field gradient coil power supply
236 Magnetic field gradient coils
238 Magnetic field generation means
240 Ultrasound transducer
242 volume filled with medium that conducts ultrasound
244 Volume adapted for receiving ultrasonic coupling medium
246 Path of ultrasound
248 MPI and/or FMPT Radio Frequency Transceiver
250 MPI and/or FMPT Transceiver coil
252 MPI and/or FMPT magnetic field gradient coil power supply
254 MPI and/or FMPT magnetic field gradient coil
300 Controlling a first heating means adapted for heating a first region of the subject such that the power directed into the first region by the heating means stays below a threshold value
302 Controlling a particle heating means adapted for heating magnetic nanoparticles within a second region
400 Receiving planning data for treatment of subject
402 Acquiring medical image data within an imaging zone
404 Generating planning data using the medical imaging data
406 Acquiring medical image data at periodic intervals
408 Identifying the location of a target region within a subject using the medical image data
410 Generating real time planning data using the location of the target region
412 Controlling the treatment of the subject using the planning data
414 Controlling a first heating means adapted for heating a first region of the subject such that the power directed into the first region by the heating means stays below a threshold value
416 Adjusting the location of the second region based upon motion and/or deformation of the target region using the real time planning data
418 Controlling the location of the second region using the magnetic field generation means 420 Controlling a particle heating means adapted for heating magnetic nanoparticles within a second region
500 System Backend and Workstation
502 Element for defining tumor volume based on prior MR or CT scan
504 Element for Defining desired Temperature Map and Dose Plan
506 HIFU Frontend
508 Element for Ultrasound Signal Generation
510 HIFU Transducer Array
512 FMPT Frontend
514 FMPT Gradient and Waveform generator
516 FMPT Gradient+RF Amplifier & Coils
600 System Backend and Workstation
602 Element for defining tumor volume based on prior MR or CT scan
604 Element for defining desired Temperature Map and Dose Plan
606 HIFU Frontend
608 Ultrasound Signal Generation
610 HIFU Transducer Array
612 FMPT Frontend
614 FMPT Gradient and Waveform generator
616 FMPT Gradient+RF Amplifier & Coils
618 Element for determining particle bio-distribution with MPI
620 Target tracking with MPI element
622 MPI Image reconstruction element
624 MPI Signal Receive Coil and Electronics
700 System Backend and Workstation
702 Element for defining tumor volume based on prior MR or CT scan
704 Element for defining desired Temperature Map and Dose Plan
706 HIFU Frontend
708 Ultrasound Signal Generation
710 HIFU Transducer Array
712 FMPT Frontend
714 FMPT Gradient and Waveform generator
716 FMPT Gradient+RF Amplifier & Coils
718 Element for determining particle bio-distribution with MPI
720 Target tracking with MPI element
722 MPI Image reconstruction element
724 MPI Signal Receive Coil and Electronics
726 MRI System
728 MRI Image Reconstruction element
730 MR Receive Coil & Electronics
732 Elements for MRI Gradient & RF Waveform Generation
734 MRI Gradient+RF Amplifiers and Coils
736 Element for Target Tracking with MRI Imaging
738 Element for 3D Temperature Monitoring with MRI

The invention claimed is:

1. A therapeutic apparatus for treating a subject comprising:
a first heating unit adapted for heating a first region of the subject,
a first control unit adapted for controlling the power directed into the first region by the first heating unit such that the power stays below a threshold value,
a particle heating unit adapted for heating magnetic nanoparticles within a second region of the subject using a time varying magnetic field,
wherein the first region includes the second region, wherein the first heating unit is an ultrasonic heating unit, wherein the threshold value is selected such that the temperature increase in the first region due to the ultrasonic heating unit does not induce cell death, wherein the second region includes at least one hyperthermia zone induced by the temperature increase in the first region due to the ultrasonic heating unit, wherein the at least one hyperthermia zone has a concentration of magnetic nanoparticles sufficient to cause a temperature increase after the ultrasonic heating which induces cell death when heated by the particle heating unit, and wherein the ultrasonic heating unit is a high intensity focused ultrasound unit,
wherein the particle heating unit modulates the magnetic field in the second zone such that it heats the magnetic nanoparticles using one of the following mechanisms: Brownian relaxation, Néel relaxation, or a combination of Brownian relaxation and Néel relaxation.

2. The therapeutic apparatus of claim 1, wherein the particle heating unit further comprises a magnetic field generation unit adapted for heating the magnetic nanoparticles using focused magnetic particle therapy, wherein the therapeutic apparatus further comprises a second control unit for controlling the particle heating unit, wherein the second control unit is adapted for controlling the location of the second region, wherein the second control unit is adapted to receive planning data for planning treatment of the subject, and wherein the therapeutic apparatus is adapted for performing therapy using the planning data.

3. The therapeutic apparatus of claim 2, wherein the magnetic field generation unit is further adapted for acquiring medical image data within an imaging zone using magnetic particle imaging, wherein the imaging zone includes the first region, and wherein the second control unit is adapted for generating planning data using the medical image data.

4. The therapeutic apparatus of claim 2, wherein the therapeutic apparatus further comprises a magnetic resonance imaging system adapted for acquiring medical image data within an imaging zone, wherein the imaging zone comprises the first region, and wherein the second control unit is adapted for generating planning data using the medical image data.

5. The therapeutic apparatus of claim 4, wherein the magnetic resonance imaging system is adapted for acquiring temperature data using magnetic resonance thermometry, wherein the medical image data comprises temperature data, wherein the first control unit is adapted for limiting the temperature in the first region using the medical image data, and wherein the second control unit is adapted for controlling the temperature in the second region using the medical image data.

6. The therapeutic apparatus of claim 3, wherein the therapeutic apparatus is adapted for acquiring medical image data at periodic intervals, wherein the therapeutic apparatus is adapted for identifying the location of a target region within the subject using the medical image data, wherein the second control unit is adapted for generating real time planning data using the location of the target region, wherein the second control unit is adapted for adjusting the location of the second region based upon motion and/or deformation of the target region using the real time planning data.

7. The therapeutic apparatus of claim 1, wherein the therapeutic apparatus is operable for treating any one of the following: tumors in an eye, tumors in the brain, tumors in nerve bundles, tumors in the spinal cord, tumors in a lung, tumors in the prostate gland, tumors adjacent to an eye, tumors adjacent to the brain, tumors adjacent to nerve bundles, tumors adjacent to a lung, tumors adjacent to the prostate gland, tumors adjacent to the wall of the bladder, tumors adjacent to the rectum, tumors adjacent to an organ boundary, multiple tumors distributed throughout the subject, tumors with multiple small foci, tumors adjacent to air tissue boundaries, or tumors adjacent to bone tissue boundaries.

8. A computer program product comprising a set of executable instructions for execution by a therapeutic apparatus for treating a subject, comprising the steps of:
controlling a first heating unit adapted for heating a first region of the subject such that the power directed into the first region by the first heating unit stays below a threshold value,
controlling a particle heating unit adapted for heating magnetic nanoparticles within a second region using a time varying magnetic field after the heating of a first region, and wherein the first region includes the second region,
wherein the first heating unit is an ultrasonic heating unit, wherein the threshold value is selected such that the temperature increase in the first region due to the ultrasonic heating unit does not induce cell death, wherein the second region includes at least one hyperthermia zone induced by the temperature increase in the first region due to the ultrasonic heating unit, wherein the at least one hyperthermia zone has a concentration of magnetic nanoparticles sufficient to cause a temperature increase which induces cell death when heated by the particle heating unit, wherein the ultrasonic heating unit is a high intensity focused ultrasound unit and wherein the particle heating unit modulates the magnetic field in the second zone such that it heats the magnetic nanoparticles using one of the following mechanisms: Brownian relaxation, Néel relaxation, or a combination of Brownian relaxation and Néel relaxation.

9. The computer program product of claim 8, wherein the particle heating unit comprises a magnetic field generation unit adapted for focused magnetic particle therapy, the computer program product further comprising the steps of:
receiving planning data for planning treatment of the subject,
controlling the treatment of the subject using the planning data, and
controlling the location of the second region using the magnetic field generation unit.

10. The computer program product of claim 9 further comprising the steps of:
acquiring medical image data within an imaging zone using magnetic particle imaging and/or magnetic resonance imaging, wherein the imaging zone includes the first region, and
generating planning data using the medical image data.

11. The computer program product of claim 10 further comprising the steps of:
acquiring medical image data at periodic intervals,
identifying the location of a target region within subject using the medical image data acquired at periodic intervals,
generating real time planning data using the location of the target region, and
adjusting the location of the second region based upon motion and/or deformation of the target region using the real time planning data.

* * * * *